(12) United States Patent
Yu et al.

(10) Patent No.: US 8,518,685 B2
(45) Date of Patent: Aug. 27, 2013

(54) ENGINEERED NITRILE HYDRATASE-PRODUCING BACTERIUM WITH AMIDASE GENE KNOCKED-OUT, THE CONSTRUCTION AND THE USE THEREOF

(75) Inventors: Huimin Yu, Beijing (CN); Yuchao Ma, Beijing (CN); Changchun Liu, Beijing (CN); Zhongyao Shen, Beijing (CN)

(73) Assignee: Tsinghua University (CN)

( * ) Notice: Subject to any disclaimer, the term of this patent is extended or adjusted under 35 U.S.C. 154(b) by 127 days.

(21) Appl. No.: 12/933,725

(22) PCT Filed: Mar. 24, 2008

(86) PCT No.: PCT/CN2008/000572
§ 371 (c)(1),
(2), (4) Date: Sep. 21, 2010

(87) PCT Pub. No.: WO2009/117843
PCT Pub. Date: Oct. 1, 2009

(65) Prior Publication Data
US 2011/0104690 A1    May 5, 2011

(51) Int. Cl.
*C12N 1/12*        (2006.01)
*C12Q 1/68*        (2006.01)

(52) U.S. Cl.
USPC ........................................ 435/252.1; 435/6.1

(58) Field of Classification Search
None
See application file for complete search history.

(56) References Cited

U.S. PATENT DOCUMENTS 6,153,415 A * 11/2000 Oriel et al. ................... 435/129
7,118,898 B1  10/2006 Aoki et al.

FOREIGN PATENT DOCUMENTS

| CN | 1340101 A | 3/2002 |
|---|---|---|
| WO | WO-2006/049618 A1 | 5/2006 |

OTHER PUBLICATIONS

Komeda et al (Journal of Biological Chemistry vol. 271, No. 26, pp. 15796-15802, 1996).*
"International Application Serial No. PCT/CN2008/000572, International Search Report mailed Dec. 25, 2008", 6 pgs.

* cited by examiner

*Primary Examiner* — Albert Navarro
(74) *Attorney, Agent, or Firm* — Schwegman Lundberg & Woessner, P.A.

(57) ABSTRACT

An engineered nitrile hydratase-producing bacterium and its construction method as well as its applications, wherein the engineered nitrile hydratase-producing bacterium is a mutant strain of an original nitrile hydratase-producing bacterium strain obtained by knocking-out or inhibiting the amidase gene in the original strain. The construction method of the engineered bacterium is to block the expression of the amidase gene by inserting the large fragment of a recombinant suicide plasmid carrying an amidase gene fragment into a wild-type strain through the homologous recombination between the recombinant suicide plasmid and the amidase gene of the wild-type strain. Compared to the corresponding wild-type bacterium strain, both the cell growth and the nitrile hydratase expression of the engineered nitrile hydratase-producing bacterium according to the invention are increased. In the process of catalyzing the hydration of acrylonitrile to produce acrylamide, the yield of the product, acrylamide, is significantly increased, while the yield of the by-product acrylic acid is significantly decreased. The engineered nitrile hydratase-producing bacterium of the present invention has wide application prospect in the production of acrylamide by microbiological process.

6 Claims, 1 Drawing Sheet

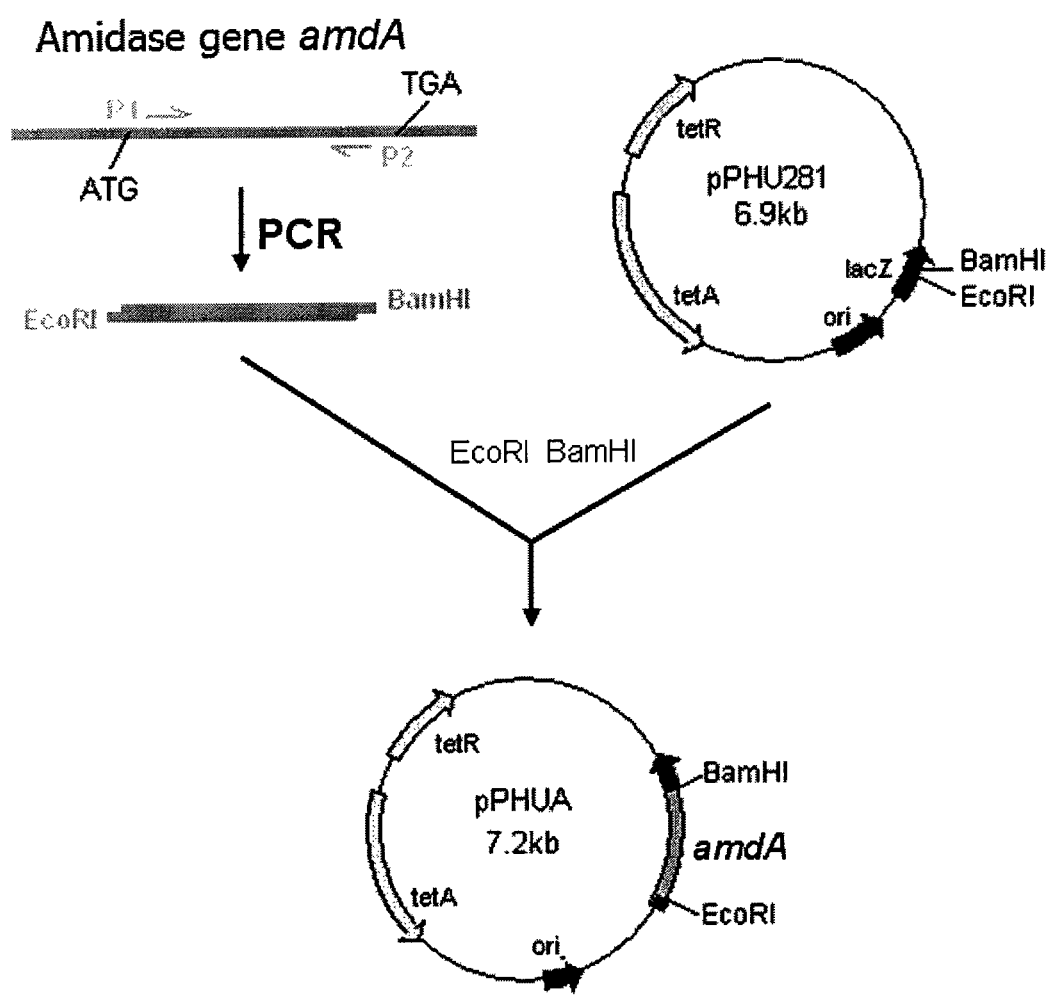

ENGINEERED NITRILE HYDRATASE-PRODUCING BACTERIUM WITH AMIDASE GENE KNOCKED-OUT, THE CONSTRUCTION AND THE USE THEREOF

FIELD OF THE INVENTION

This invention relates to the field of industrial microbiology, specifically to an engineered nitrile hydratase-producing bacterium with the amidase gene knocked-out, and the construction thereof as well as the use of the engineered nitrile hydratase-producing bacterium in acrylamide production.

BACKGROUND ART

Polyacrylamide (PAM) is referred to as an "additive for different purposes" and has wide applications in many industrial fields, such as tertiary oil recovery, water treatment, paper making, mining, metallurgy, coal cleaning and manufacture of super water-absorbent resins and so on. The monomer of polyacrylamide is acrylamide (with a molecular formula of $C_3H_5NO$, and a structural formula of $H_2C=CHCONH_2$), which is generally produced through catalytic hydration using acrylonitrile as raw material. The hydration method for acrylamide experienced three stages of development, i.e. sulfuric acid catalysis, copper catalysis and microbiological process. Currently, the microbiological process has become the primary method of acrylamide production due to its advantages, such as normal temperature and normal pressure for the reaction, low energy consumption, simple operation, safety, high conversion rate of acrylonitrile, high concentration and purity of the product, etc.

The method for producing acrylamide using microbiological process mainly focuses on screening and domestication of bacterial strains, as well as the establishment and optimization of the manufacture techniques.

For the finding, domestication, mutagenesis and reconstruction of the production strains, Hideaki Yamada group in Japan discloses a wild-type *Rhodococcus rhodochrous* J-1 in the patent with the title "BIOLOGICAL PRODUCTION METHODS OF AMIDES " (Chinese Patent No.: ZL88106735). Nippon Chemical Industrial Co., Ltd. discloses *Rhodococcus* sp. S-6, *Arthrobacter oxydans* and *Microbacterium flavum* in the patent with the title "PREPARATION OF AMIDES USING MICROORGANISMS" (Chinese Patent No.: ZL86100062). CIBA SPECIALTY CHEMICALS WATER TREATMENTS LIMITED discloses *Rhodococcus rhodochrous* NCIMB 41164 strain and its mutants in the patent with the title "STRAIN OF RHODOCOCCUS RHODOCHROUS NCIMB 41164 *AND ITS USE AS PRODUCER OF NITRILE HYDRATASE*" (Chinese Patent Application No.: 200480035487.1). Ashland Licensing and Intellectual Property LLC discloses *Rhodococcus rhodochrous* strain M33 in the patent with the title "METHOD FOR CULTURING THE NITRILE HYDRATASE-PRODUCING STRAIN RODOCOCCUS RHODOCHROUS M33" (Chinese Patent Application No.: 200480043243.8). Shanghai Pesticide Research Institute describes a wild-type *Corynebacterium propinquum* and its domesticated strain for acrylamide production by microbiological process in the patent with the title "PRODUCTION OF ACRYLAMIDE WITH MICROBIAL CATALYSIS" (Chinese Patent Application No.: 03115536.7). Tsinghua University discloses a method of obtaining a tolerant nitrile hydratase in the patent with the title "THE ORIENTATION CULTURE METHOD FOR IMPROVING THE PRODUCT-TOLERANCE OF NITRILE HYDRATASE" (Chinese Patent No.: ZL 03130658).

In recent years, in the gene research and engineering on the conversion of acrylonitrile to acrylamide, Japanese Mitsubishi Chemical Corporation filed a patent with the title "NOVEL PROTEIN WITH NITRILE HYDRATASE ACTIVITY AND THE GENE ENCODING THE SAME" for the nitrile hydratase gene and the protein from the genus *Rhizobium* (Chinese Patent Application No.: 93106122.9). Mitsui Chemicals Co., Ltd. filed patents with the titles "A PROTEIN INVOLVED IN ACTIVATION OF NITRILE HYDRATASE AND THE GENE ENCODING THE SAME" (Chinese Patent No.: ZL99106291.4) and "NOVEL NITRILE HYDRATASE" (Chinese Patent No.: 02156180.X), respectively, for a nitrile hydratase protein and its encoding gene from *Pseudonocardia thermophila* JCM3095, and also investigated the expression of the gene in the recombinant *Escherichia coli*. Degussa A G filed a patent with the title "NITRILE HYDRATASE OF RHODOCOCCUS" (Chinese Patent Application No.: 200580008206.8), and Mitsubishi Rayon Co., Ltd. filed a patent with the title "IMPROVED NITRILE HYDRATASE" (Chinese Patent Application No.: 200580016665.0), disclosing a method for improving the thermotolerance of nitrile hydratase by site-directed mutagenesis. Tsinghua University obtained a nitrile hydratase gene from *Nocardia* sp. and filed a patent with the title "A NITRILE HYDRATASE, ITS ENCODING GENE AND THE USE THEREOF" (Chinese Patent No.: ZL 200410042576.0), wherein the mutation and high expression of the gene in recombinant *Escherichia coli* were further studied.

In addition to nitrile hydratase, in the strains that produce acrylamide using nitrile hydratase, there is amidase which can further convert acrylamide produced by nitrile hydratase catalysis into by-product acrylic acid, thereby seriously affecting the quality and yield of acrylamide, as well as increasing the purification difficulty and the production costs. Nitrile hydratase and amidase genes are usually organized in a same large gene cluster (such as in *Pseudomonas chlororaphis* B23, *Rhodococcus* sp. N771, *Rhodococcus rhodochrous* J1, *Rhodococcus* sp. RHA1 and *Bacillus* sp. BR449) or in independent gene clusters (such as in *Nocardia farcinica* IFM 10152 and *Rhodococcus rhodochrous* sp. M8) in the chromosomal genome of the strains (Brandao et al., Applied and Environmental Microbiology, 2003, 69 (10): 5754-5766; Ryabchenko et al., Genetika, 2006, 42(8):1075-82.). If the amidase gene is inhibited or knocked-out, the by-product acrylic acid can be avoided to be produced in a large amount during the production of acrylamide, thereby significantly reducing the burden of isolation and purification in the refining unit and the production cost.

In the present invention, the amidase gene is knocked-out from a nitrile hydratase-producing bacterial strain, so as to suppress the generation of by-product acrylic acid during the production of acrylamide.

SUMMARY OF THE INVENTION

The first object of this invention is to provide an engineered nitrile hydratase-producing bacterium with the amidase gene knocked-out.

The second object of the present invention is to provide a construction method for the above engineered nitrile hydratase-producing bacterium.

The third object of the present invention is to provide the use of the above engineered nitrile hydratase-producing bacterium in the production of acrylamide.

In order to achieve these above objects, the technical solutions adopted herein are as follow.

The engineered nitrile hydratase-producing bacterium used herein refers to a mutant strain of an original nitrile hydratase-producing bacterial strain obtained by inhibiting or knocking-out the amidase gene in the original nitrile hydratase-producing bacterial strain.

The above original nitrile hydratase-producing bacterial strain refers to a bacterial strain, such as *Rhodococcus* spp., *Nocardia* spp., *Pseudonocardia thermophila*, *Bacillus subtilis*, *Pseudomonas* spp., *Corynebacterium propinquum* or other nitrile hydratase producing Gram-positive bacteria, that can express nitrile hydratase gene and use the nitrile hydratase to produce acrylamide.

The above engineered nitrile hydratase-producing bacterium refers to *Rhodococcus ruber* TH3 (amdA$^-$) or its mutant strain. *Rhodococcus ruber* TH3 (amdA$^-$) was deposited in China General Microbiological Culture Collection Center, Institute of Microbiology, Chinese Academy of Sciences, Datun Road, Chaoyang District, Beijing, China 100101 on Feb. 27, 2008 under the deposit number CGMCC No. 2381. *Rhodococcus ruber* TH3 (amdA$^-$) is an engineered nitrile hydratase-producing bacterium obtained by knocking out the amidase gene from the starting bacterium strain *Rhodococcus ruber* TH. The expression of the amidase gene in the strain is blocked, and this strain carries the tetracycline resistance gene.

The starting bacterial strain of the above *Rhodococcus ruber* TH3 (amdA$^-$) is *Rhodococcus ruber* TH, which was also deposited in China General Microbiological Culture Collection Center, Institute of Microbiology, Chinese Academy of Sciences, Datun Road, Chaoyang District, Beijing, China 100101 on Feb. 27, 2008 under the deposit number CGMCC No. 2380.

The selection procedure of the *Rhodococcus ruber* TH comprises:

(1) 25 soil samples in total were collected from ponds, roadsides, treesides and chemical plants in Tsinghua University campus in Beijing, Summer Palace in Beijing, Nantong in Jiangsu province, etc. One gram of each sample was taken and dissolved in 10 ml sterile water. Then the aqueous portions were transferred into 40 ml enrichment medium (medium composition: Glucose 10 g/L, $K_2HPO_4$ 0.8 g/L, $KH_2PO_4$ 3.3 g/L, $MgSO_4.7H_2O$ 0.2 g/L, NaCl 1 g/L, $FeSO_4.7H_2O$ 10 mg/L, $CaCl_2$ 15 mg/L, acrylonitrile 1 g/L, pH 7.0-7.2) sterilized at 121° C. for 15 min, and were cultured at 28° C. in a shaker at 200 rpm for 3 to 4 days. 1 ml of the culture broth of the bacterial solutions was taken for inoculating the fresh enrichment medium, and the enrichment was performed three times in total. The enrichment culture broth was diluted to different concentrations, and 200 μL was then plated on a plate with solid enrichment medium (solid enrichment medium was prepared by adding 15 g/L agar powder into the above enrichment medium). After 2-3 days culture in an incubator at 28° C., single colonies with different morphologies appeared in the plate. Single colonies with different morphologies were picked for shaking-flask culture (medium composition: Glucose 20 g/L, yeast extract 5.0 g/L, urea 7.5 g/L, $KH_2PO_4$ 0.75 g/L, $K_2HPO_4$ 0.75 g/L, $MgSO_4.7H_2O$ 1.0 g/L, Monosodium Glutamate, 0.75 g/L, $CoCl_2$ 0.06 mM, pH 7.5, dissolved in water) at 28° C. in a shaker at 200 rpm for 72 hours. 1 ml of the broth sample was taken and centrifuged at 8000 rpm for 3 min, and then resuspended in equal volume of water. Acrylonitrile was added to start the hydration, and the hydration results were determined by gas chromatography (WANG Tie-gang, LUO Hui, etc., Quickly quantitative detection of acrylonitrile's biocatalysis products by gas chromatography. *Chinese journal of analysis laboratory*, 2007, 26 (1): 54-57). The strains capable of producing acrylamide are target strains.

(2) A colony of circular morphology, regular edge, orange-red color, and smooth surface was selected out from the above samples, and the detection results indicated that this strain had a high nitrile hydratase activity. The sequences of the primers 16SP1 and 16SP2 designed for PCR amplification so as to obtain the sequence of 16S rDNA of the strain are as follow:

16SP1: 5'-AGAGTTTGATCCTGGCTCAGAACGAACGCT-3' (SEQ ID NO: 4),

16SP2: 5'-TACGGCTACCTTGTTACGACTTCACCCC-3' (SEQ ID NO: 5),

The 16S rDNA sequence of 1487 bp in length (SEQ ID NO: 6) was obtained by sequencing.

(3) The above 16S rDNA sequence shows a high homology with that of *Rhodococcus* when searching and comparing against NCBI gene sequence database. Its homology to *R. ruber* DSM43338$^T$ is 99%, to *R. rhodochrous* DSM 43241$^T$ is 97%, to *R. coprophilus* DSM43347$^T$ is 96% and to *R. rhodnii* DSM43336$^T$ is 96%. This indicates that this strain belongs to the genus *Rhodococcus* and is different from other strains. Thus, this is a new strain and then designated as *Rhodococcus ruber* TH.

The present invention provides a method of constructing an engineered nitrile hydratase-producing bacterium by knocking-out amidase gene, comprising mainly inserting an amidase gene fragment (SEQ ID NO: 3) to be knocked-out into a suicide plasmid vector by single cross-over homologous recombination to construct a recombinant suicide plasmid, then transforming a host bacterium with the recombinant suicide plasmid by electroporation for homologous exchange, and obtaining an engineered bacterium by resistance selection in which the amidase gene is blocked after gene homologous recombination.

The present invention provides a method for constructing an engineered nitrile hydratase-producing bacterium with amidase gene knocked-out, comprising steps:

(1) performing PCR amplification with primers P1 and P2 using the genome DNA of an original bacterium strain carrying amidase gene as the template, and recovering the amplified fragment, wherein the sequences of the primers are as follow:

Upstream primer P1: 5'-TCAGAATTCGCGGTGGTCAACTACAAGA-3' (the EcoR I restriction sites are underlined) (SEQ ID No: 1), Downstream primer P2: 5'-GATGGATCCAACAGGTGATTCTGGGACTG-3' (the BamH I restriction sites are underlined) (SEQ ID No: 2).

(2) digesting the amplified fragment obtained in step (1) and a plasmid vector, respectively, with EcoRI and BamHI at 36-38° C. for 4-6 h, purifying the digested products and then ligating with T4 DNA ligase at 3-5° C. for 14-16 h to obtain ligation reactants;

(3) transforming competent cells of *E. coli* JM109 with the ligation reactants, plating the transformed cells on LB solid medium, selecting out and culturing positive clones, extracting a small amount of plasmids for verification by enzyme cleavage, and obtaining a recombinant suicide plasmid carrying an amidase gene fragment;

(4) transforming the original bacterium strain with the recombinant suicide plasmid by electroporation;

(5) obtaining an engineered nitric hydratase-producing bacterium in which the expression of amidase gene is blocked by plating the transformed bacterium strain in step (4) on LB solid medium supplemented with an antibiotic and selecting out positive colony.

The original bacterium strain mentioned in above steps (1) and (4) refers to a strain selected from *Rhodococcus, Nocardia, Pseudonocardia thermophila, Bacillus subtilis, Pseudomonas, Corynebacterium propinquum* or other nitrile hydratase-producing Gram-positive bacteria.

The plasmid vector mentioned in above step (2) may be pPHU281 (Hübner P, etc. *Mol Microbiol*. 1993; 10: 123-132) or its derived plasmid, one of the pUC or pET series plasmid vectors for *E. coli*.

The purification of the enzymatically cleaved products in above step (2) can be performed using PCR product recovery kit or other commonly used purification means in molecular cloning.

The amidase gene fragment mentioned in above step (3) refers to a DNA sequence or a fragment containing the sequence as shown in SEQ ID NO: 3, an extension fragment of the sequence as shown in SEQ ID NO: 3, a part of the sequence as shown in SEQ ID NO: 3, or having more than 70% homology with the sequence as shown in SEQ ID NO: 3.

The amidase gene carried in the recombinant suicide plasmid mentioned in above step (3) can effect a single cross-over homologous recombination with the amidase gene in the host bacterium. The large fragment of the recombinant suicide plasmid carrying an antibiotic resistance marker is inserted within the amidase gene of the host bacterium, thereby blocking the expression of the amidase gene.

The selection marker gene used in above step (5) can be tetracycline resistance gene, kanamycin resistance gene, erythromycin resistance gene, chloramphenicol resistance gene or other antibiotic resistance genes.

*Rhodococcus ruber* TH3 (amdA⁻) is constructed as described above, wherein the original strain is *Rhodococcus ruber* TH, the plasmid vector is pPHU281, and the obtained recombinant suicide plasmid is pPHUA.

The composition and the preparation of the above mentioned LB solid medium refer to "Guide to molecular cloning" by J Sambrook and D W Russell.

The recombinant suicide plasmid described herein cannot replicate and is not inheritable in the host cell due to the absence of any replicon of the host bacterium, and thus will be lost very soon. The amidase gene carried in the suicide plasmid can effect a homologous recombination with the host chromosome in a short time, and the resistance gene in the plasmid is inserted within the amidase gene of the chromosome, leading to blockage of the expression of the amidase gene of the host. Those suicide plasmids that do not effect the homologous recombination are lost during the subsequent cell culture and thus will not affect the performance of the strain.

Use of the above engineered nitrile hydratase-producing bacterium in the production of acrylamide A method for producing acrylamide using the above engineered nitrile hydratase-producing bacterium in which the amidase gene is knocked out is provided, comprising the following steps.

(1) The engineered nitrile hydratase-producing bacterium stored at 4° C. is inoculated into seed-culture medium, and cultured for 32-56 hours at 28-30° C. on a shaker at 150-250 rpm to obtain a seed broth of the engineered nitrile hydratase-producing bacterium. The composition and proportion of the seed culture medium are as follow: Glucose 10-30 g/L, Yeast Extracts 1-5 g/L, peptone 5-10 g/L, $KH_2PO_4$ 0.5-0.75 g/L, $K_2HPO_4$ 0.5-0.75 g/L, $MgSO_4.7H_2O$ 0.5-1.0 g/L, pH 7-8, tetracycline: 10-60 mg/L, and the rest is water.

(2) At 0.5-10% volume ratio, the seed broth obtained in step (1) is inoculated into a shaking flask or a fermentor containing fermentation medium, and then cultured at 28-30° C., pH7.5-8.5 for 36-72 hours to obtain the fermentation broth. The composition of said fermentation medium is as follow: glucose 10-40 g/L, yeast extract 5.0-10.0 g/L, urea 5.0-10.0 g/L, $KH_2PO_4$ 0.5-1.0 g/L, $K_2HPO_4$ 0.5-1.0 g/L, $MgSO_4.7H_2O$ 0.5-1.5 g/L, Monosodium Glutamate 0.5-1.5 g/L, $CoCl_2$ 0.04-0.12 mM, pH 7.5-8.5, and the rest is water.

(3) At 5-20% volume ratio, the engineered nitrile hydratase-producing bacterial cells obtained in step (2) are resuspended in water. The enzymatic activity of the resuspension is in a range of 1500-4000 U/ml.

(4) The cell resuspension obtained in step (3) is transferred into a hydration reactor or a conical flask. Then acrylonitrile is continuously fed into the reactor or the flask, and the reaction is performed under the condition of 15-30° C., pH 6.5-8.5 for 1-6 hours. The concentration of acrylamide is determined. The hydration reaction is terminated when the concentration of acrylamide reaches 20-50% (W/N) and acrylamide is thus obtained.

The reaction temperature of step (4) in the above method may be adjusted with liquid ammonia, low temperature freezing salt water, cooling water or cold ethanol etc.

The advantages and beneficial effects of the present invention are as follow. (1) The cell growth and nitrile hydratase expression of the engineered nitrile hydratase-producing bacterium of the invention are not affected substantially by the knockout of amidase gene, in contrary increased slightly. (2) During the catalytic production of acrylamide using the engineered nitrile hydratase-producing bacterium of the present invention, the production of by-product acrylic acid is greatly reduced, e.g. the production of by-product acrylic acid using *Rhodococcus* in which the amidase gene is knocked-out obtained in the invention is reduced by about 90% compared to the wild-type *Rhodococcus ruber* TH. (3) Using the engineered bacterial strain of the invention for producing acrylamide, the hydration temperature is increased, the burden of the refining is reduced, the production cost is thus decreased, and the quality of the product is high. Thus it is suitable for industrial production.

BRIEF DESCRIPTION OF THE FIGURE

FIG. 1 The schematic illustration of the construction of the recombinant suicide plasmid pPHUA that carries an amidase gene fragment.

MODE OF CARRYING OUT THE INVENTION

EXAMPLE 1

Construction of the Recombinant Suicide Plasmid pPHUA Carrying an Amidase Gene Fragment Using the genomic DNA of *Rhodococcus ruber* TH as the template, PCR amplification was carried out with upstream primer P1: 5'-TCA GAATTCGCGGTGGTCAACTACAAGA-3'(the EcoRI restriction sites are underlined) and downstream primer P2: 5'-GATGGATCCAACAGGTGATTCTGGGACTG-3' (the BamHI restriction sites are underlined). PCR amplification condition was: pre-denaturation at 95° C. for 5 min; then 30 cycles of amplification (95° C. for 30 s; 60° C. for 30 s; 72° C. for 1 min), and final extension at 72° C. for 10 min. An amidase gene fragment (SEQ ID NO: 3) obtained by PCR amplification and the suicide plasmid pPHU281 (Hübner P, Masepohl B, et al. Mol Microbiol. 1993; 10: 123-132) were digested with both EcoRI and BamHI (TAKARA BIOTECHNOLOGY (DALIAN) CO., LTD) at 37° C. for 4 h. The digested products were purified using PCR products recovery kit (TIANGEN BIOTECH (Beijing) Co., Ltd.), and then ligating using T4 DNA ligase (Promega Corporation) at 4° C. for 16 h. The competent cells of the host E. coli JM109 (TIANGEN BIOTECH (Beijing) Co., Ltd.) were transformed with the products of ligation reaction, and the positive clones were selected in LB plate suplemented with tetracycline. Small amount of plasmids were extracted after overnight culture in LB medium at 37° C. for enzymatic cleavage and electrophoresis verification. The recombinant suicide plasmid pPHUA that carries an amidase gene fragment was thus obtained (see FIG. 1).

EXAMPLE 2

Construction of the Recombinant *Rhodococcus ruber* TH3 (amdA⁻)

*Rhodococcus ruber* TH competent cells were transformed with the recombinant suicide plasmid pPHUA carrying the amidase gene fragment constructed as described in example 1 by electroporation, and the genetic recombinant *Rhodococcus* was obtained by tetracycline resistance selection. The *Rhodococcus ruber* competent cells were prepared according to the standard protocol of the Gram-positive bacterial competent cells as described in "Guide to Molecular Cloning" (J. Sambrook, D W Russell a). 1 μl of the purified plasmid was placed in a 1.5 ml centrifuge tube, placed together with 0.1 CM electroporation cuvette on ice for pre-cooling. 50 μl prepared competent cells were transferred into the tube and carefully mixed, kept on ice for 10 min. The electroporation apparatus was turned on and the voltage was set at 1250 V. The mixture of the suicide plasmid and the competent cells were then transferred into the pre-cooled electroporation cuvette, gently tapped to enable the mixture drop into the bottom of the cuvette, being aware that there should be no air bubbles in the mixture. The cuvette was placed into the electroporation apparatus and the pulse button was then pressed. After hearing the beep sound, 800 μl of liquid SOC medium (the formulation can be seen in "Guide to Molecular Cloning") was added immediately into the cuvette. After resuspending the cells, the resuspension was transferred into a 1.5 ml centrifuge tube. The culture was done at 28° C. for 2 h in a 220 rpm shaker. 200 μl bacterial broth were taken and plated on a plate with solid LB medium containing 14 μg/ml tetracycline. After culturing the plate in an incubator at 28° C. for 48 hours, single colonies of recombinant *Rhodococcus* appeared. 20 single colonies were picked out for culture and induced for nitrile hydratase expression, wherein one recombinant *Rhodococcus* strain with highest expression level of nitrile hydratase but lowest amidase activity was selected for further separate culture. Genomic DNA extraction Kit (TIANGEN BIOTECH (Beijing) Co., Ltd.) was used to extract genomic DNA, which was then used as the template for PCR amplification using the primers and conditions as described in Example 1. It was confirmed by the results of routine agarose gel electrophoresis that the large fragment of the suicide plasmid was correctly inserted into the amidase gene. Finally, the recombinant *Rhodococcus ruber* with amidase gene knocked-out was designated as *Rhodococcus ruber* TH3 (amdA⁻).

EXAMPLE 3

Cell Growth and Nitrile Hydratase Expression of TH3(amdA⁻) Cells with Amidase Gene Knocked-Out The recombinant *Rhodococcus ruber* TH3 (amdA⁻) obtained in Example 2 in which the amidase gene was knocked-out and the wild-type *Rhodococcus ruber* TH were cultured in parallel. Orange, smooth and moist single colonies were picked out from the TH3 (amdA⁻) and TH plates with LB solid medium, then inoculated into 50 ml of seed medium (500 ml flask) and cultured at 28° C. for 48 h in a 200 rpm shaker (The composition of the seed medium: glucose 20 g/L, Yeast Extract 5 g/L, peptone 10 g/L, $KH_2PO_4$ 0.5 g/L, $K_2HPO_4$ 0.5 g/L, $MgSO_4 \cdot 7H_2O$ 0.5 g/L, pH 7.5, and the rest is water). At 10% volume ratio, the culture broth was inoculated into 50 ml (500 ml flask) fermentation medium (Glucose 20 g/L, yeast extract 5.0 g/L, urea 7.5 g/L, $KH_2PO_4$ 0.75 g/L, $K_2HPO_4$ 0.75 g/L, $MgSO_4 \cdot 7H_2O$ 1.0 g/L, Monosodium Glutamate 0.75 g/L, $CoCl_2$ 0.06 mM, pH 7.5, and the rest is water). The flask were then cultured in batches at 28° C. for 48 h on a 200 rpm shaker. The test results showed that the activity of nitrile hydratase in TH3 (amdA⁻) was 3820 U/ml, while 3060 U/ml in TH, and the optical density at 460 nm was 41.8 for TH3 (amdA⁻), while 38.2 for TH. Further fed-batch culture was carried out for TH3 (amdA⁻), supplementing glucose to a final concentration of 10 g/L at 40 h, 48 h and 60 h, respectively and adjusting pH to pH 7.0, and the cultur continued until 74 h. The nitrile hydratase activity of TH3 (amdA⁻) reached up to 9726 U/ml and the cell density at $OD_{460}$ reached 71.5. This indicated that both the growth and the nitrile hydratase expression of TH3 (amdA⁻) were better than wild-type strain TH, wherein the nitrile hydratase activity was determined by standard gas chromatography internal standard method (WANG Tie-gang, LUO Hui, etc., Quickly quantitative detection of acrylonitrile's biocatalysis products by gas chromatography. Chinese journal of analysis laboratory, 2007, 26 (1): 54-57). Internationally one unit of enzyme activity is defined as the amount of enzyme required to catalyze the formation of 1 μmol acrylamide per minute: 1 μmol acrylamide/(min·ml bacterial broth)=1 U/ml.

EXAMPLE 4

Shaking-Flask Production of Acrylamide Using TH3 (amdA⁻)

The TH3 (amdA⁻) and TH cells obtained in Example 3 were respectively centrifuged at 8000 rpm for 10 min, and the pellets were harvested to obtain TH3 (amdA⁻) and TH cells respectively. At 5% volume ratio, cell resuspensions were formulated and placed in 300 ml conical flasks. The enzyme activity of the resuspension was 1800 U/ml, pH7.0. 500 μl acrylonitrile was fed into the resuspension every 30 min, and the hydration reaction was carried out at 18° C. on a low temperature refrigeration shaker. The hydration reaction was stopped after 6 h. The concentrations of acrylonitrile, acrylamide and acrylic acid were measured by gas chromatography. The results showed that no acrylonitrile was remained in the TH reaction system. The yield of the product acrylamide was 93.76 g/L, and the yield of by-product acrylic acid was 14.12 g/L. No acrylonitrile was remained in the TH3 (amdA⁻) reaction system. The yield of the product acrylamide was 115.68 g/L, which was 23% higher than TH, and the yield of by-product acrylic acid was 1.97 g/L, which was 86% lower than TH. This indicated that the amidase gene was significantly inhibited.

EXAMPLE 5

Production of Acrylamide Using TH3 (amdA⁻) with the Amidase Gene Knocked-Out in a Reactor Cell suspension was formulated in a stirred-tank jacketed reactor (Shanghai Lianhuan Bio-engineering Equipment Co. LTD) according to a similar method as described in Example 4, and the hydration reaction was carried out for TH3 (amdA⁻). The amount of free cells in the reaction system was 13 g dry cell weight/L. The volume fraction of the bacterial suspension was 8% and the rest was water, pH7.0. The nitrile hydratase activity in the resuspension was 2500 U/ml. Acrylonitrile was continuously feeding into the reactor, and the feeding rate was adjusted to maintain the reaction temperature at 20° C. The reaction was carried out for 3 h, and then the concentrations of acrylamide and acrylic acid were measured as 345.6 g/L and 0.14 g/L, respectively. This indicated that the expression of the amidase gene was inhibited.

```
                           SEQUENCE LISTING

<160> NUMBER OF SEQ ID NOS: 6

<210> SEQ ID NO 1
<211> LENGTH: 28
<212> TYPE: DNA
<213> ORGANISM: Artificial
<220> FEATURE:
<223> OTHER INFORMATION: Synthetic upstream primer for amplifying
      amidase gene

<400> SEQUENCE: 1
tcagaattcg cggtggtcaa ctacaaga                                           28

<210> SEQ ID NO 2
<211> LENGTH: 29
<212> TYPE: DNA
<213> ORGANISM: Artificial
<220> FEATURE:
<223> OTHER INFORMATION: Synthetic downstream primer for amplifying
      amidase gene

<400> SEQUENCE: 2
gatggatcca acaggtgatt ctgggactg                                          29

<210> SEQ ID NO 3
<211> LENGTH: 785
<212> TYPE: DNA
<213> ORGANISM: Rhodococcus ruber

<400> SEQUENCE: 3
gcggtggtca actacaagat gccgcgactg cacaccaagg cggacgtcct cgagaacgcg        60
cgagcgattg cgaagatggt ggtcggcatg aaggcgggcc ttcccggtat ggatctcgtt       120
gtgttcccgg agtattcgac tatgggaatc atgtatgaca cgacgagat gtatgccacc       180 gcggcaacga ttcccgggga cgagaccgac atctttgcgc aggcatgccg cgacgcgaag      240
acgtggggtg tcttctcgat caccggcgag cgccatgagg atcacccgaa caagcccccc      300
tacaacacgc tcgtgctgat caacgatcag ggtgagatcg tgcagaagta ccgaaagatc      360
ctcccgtgga ccccgatcga aggttggtat cccggtggcc agacctatgt gaccgacggc      420
cctaaaggac tcaagatctc gctgatcatc tgcgacgacg gcaactaccc ggaaatctgg      480
cgcgattgcg cgatgaaagg tgctgagttg atcgttcgtc cgcaaggcta catgtacccg      540
tcgaaggaac aacaggtgct gatggcgaag gccatggcct gggcaaacaa ctgttacgtc      600
gcggtcgcca acgccactgg gttcgatggt gtctactcgt acttcggaca tagccgccatc     660 atcggattcg acggccgcac gttgggcgaa tgcgcgagg aagactacgg cgtccagtac      720
gcacagctgt cgctgtccac gatccgagac gcccgagcaa acgaccagtc ccagaatcac      780
``` ctgtt                                                                  785

<210> SEQ ID NO 4
<211> LENGTH: 30
<212> TYPE: DNA
<213> ORGANISM: Artificial
<220> FEATURE:
<223> OTHER INFORMATION: Synthetic upstream primer for amplifying 16S
      rDNA of Rhodococcus ruber TH

<400> SEQUENCE: 4
agagtttgat cctggctcag aacgaacgct                                        30

<210> SEQ ID NO 5
<211> LENGTH: 28
<212> TYPE: DNA
<213> ORGANISM: Artificial
<220> FEATURE:
<223> OTHER INFORMATION: Synthetic downstream primer for amplifying 16S
      rDNA of Rhodococcus ruber TH

<400> SEQUENCE: 5
tacggctacc ttgttacgac ttcacccc                                          28

<210> SEQ ID NO 6
<211> LENGTH: 1487
<212> TYPE: DNA
<213> ORGANISM: Rhodococcus ruber

<400> SEQUENCE: 6
agagtttgat cctggctcag aacgaacgct ggcggcgtgc ttaacacatg caagtcgaac       60
gatgaagccc agcttgctgg gtggattagt ggcgaacggg tgagtaacac gtgggtgatc      120
tgccctgcac ttcgggataa gcctgggaaa ctgggtctaa taccggatag gacctcggga      180
tgcatgtccc ggggtggaaa ggttttccgg tgcaggatgg gcccgcggcc tatcagcttg      240
ttggtggggt aacggcccac caaggcgacg acgggtagcc ggcctgagag ggcgaccggc      300
cacactggga ctgagacacg gcccagactc ctacgggagg cagcagtggg gaatattgca      360
caatgggcgc aagcctgatg cagcgacgcc gcgtgaggga tgacggcctt cgggttgtaa      420
acctctttca gtaccgacga agcgcaagtg acggtaggta cagaagaagc accggccaac      480
tacgtgccag cagccgcggt aatacgtagg gtgcgagcgt tgtccggaat tactgggcgt      540
aaagagctcg taggcggttt gtcgcgtcgt ctgtgaaaac ccgcagctca actgcgggct      600
tgcaggcgat acgggcagac ttgagtactg caggggagac tggaattcct ggtgtagcgg      660
tgaaatgcgc agatatcagg aggaacaccg gtggcgaagg cgggtctctg gcagtaact       720 gacgctgagg agcgaaagcg tgggtagcga acaggattag ataccctggt agtccacgcc      780
gtaaacggtg ggcgctaggt gtgggtttcc ttccacggga tccgtgccgt agctaacgca      840
ttaagcgccc cgcctgggga gtacggccgc aaggctaaaa ctcaaaggaa tcgacggggg      900
cccgcacaag cggcggagca tgtggattaa ttcgatgcaa cgcgaagaac cttacctggg      960
tttgacatac accggaccgc cccagagatg gggtttccct tgtggtcggt gcacaggtgg     1020
tgcatggctg tcgtcagctc gtgtcgtgag atgttgggtt aagtcccgca acgagcgcaa     1080
cccttgtcct gtgttgccag cacgtaatgg tgggactcg caggagactg ccggggtcaa      1140
ctcggaggaa ggtggggacg acgtcaagtc atcatgcccc ttatgtccag ggcttcacac     1200
atgctacaat ggccggtaca gagggctgcg ataccgcgag gtggagcgaa tcccttaaag     1260
ccggtctcag ttcggatcgg ggtctgcaac tcgacccat gaagtcggag tcgctagtaa      1320

```
tcgcagatca  gcaacgctgc  ggtgaatacg  ttcccgggcc  ttgtacacac  cgcccgtcac    1380
gtcatgaaag  tcggtaacac  ccgaagccgg  tggcctaacc  cctcgtggga  gggagccgtc    1440
gaaggtggga  tcggcgattg  gggtgaagtc  gtaacaaggt  agccgta                   1487
```

The invention caimed is:

1. An engineered nitrile hydratase producing bacterium, wherein the engineered nitrile hydratase producing bacterium is a mutant strain of an original nitrile hydratase producing bacterium strain obtained by knocking-out or inhibiting amidase gene in the original nitrile hydratase producing bacterium, wherein said original bacterium strain is selected from the genus *Rhodococcus*, characterized in that said engineered bacterium is *Rhodococcus ruber* TH3 (amdA⁻), deposited in China General Microbiological Culture Collection Center under a deposit number CGMCC No. 2381.

2. The engineered nitrile hydratase producing bacterium of claim 1, characterized in that the original strain of said *Rhodococcus ruber* TH3 (amdA⁻) is *Rhodococcus ruber* TH which is deposited in China General Microbiological Culture Collection Center under a deposit number CGMCC No. 2380.

3. A method for constructing the engineered nitrile hydratase producing bacterium of claim 1, comprising the steps:

(1) performing PCR amplification using P1 and P2 as primers with the genomic DNA of the original strain carrying the amidase gene as the template and recovering the amplified fragment, wherein the primers are:
upstream primer P1: 5'-TCAGAATTCGCGGTGGTCAAC-TACAAGA-3' (SEQ ID NO:1) and downstream primer P2: 5'-GATGGATCCAACAGGTGATTCTGGGACTG-3' (SEQ ID NO:2);

(2) digesting the amplified fragment obtained in step (1) and a plasmid vector with both EcoRI and BamHI at 36-38° C. for 4-6 h, purifying the digested products and obtaining a ligation product by performing a ligation reaction with T4 DNA ligase at 3-5° C. for 14-16 h, (3) transforming competent cells of *Escherichia coli* JM109 with the ligation product in step (2), plating transformants on a plate with LB solid medium, picking out positive clones for culturing, extracting a small amount of plasmids for verification through enzyme digestion, and obtaining a recombinant suicide plasmid carrying the amidase gene fragment, (4) transforming the original strain with the recombinant suicide plasmid carrying the amidase gene fragment in step (3) by electroporation, (5) obtaining an engineered nitrile hydratase producing bacteria in which the expression of the amidase gene is blocked by plating the transformed strain in step (4) on a plate with LB solid medium supplemented with an antibiotic and selecting out positive colony.

4. The method of claim 3, characterized in that said plasmid vector in step (2) is pPHU281, or is a plasmid of E. coli pUC series or pET series.

5. The method of claim 4, characterized in that said amidase gene fragment in step (3) is a DNA sequence or fragment thereof containing the DNA sequence as set forth in SEQ ID NO: 3, an extension fragment of the DNA sequence as set forth in SEQ ID NO: 3, a part of the DNA sequence as set forth in SEQ ID NO: 3, or having more than 70% homology with SEQ ID NO: 3.

6. The method of claim 5, characterized in that said marker gene for selection in step (5) is tetracycline resistance gene, kanamycin resistance gene, erythromycin resistance gene, chloramphenicol resistance gene or another antibiotic resistance gene.

* * * * *